(12) United States Patent
Wong et al.

(10) Patent No.: US 12,274,476 B2
(45) Date of Patent: Apr. 15, 2025

(54) BONE FIXATION DEVICE

(71) Applicant: WRIGHT MEDICAL TECHNOLOGY, INC., Memphis, TN (US)

(72) Inventors: Kian-Ming Wong, Lakeland, TN (US); Freddie Lobianco, Gulfport, MS (US); Jeffrey Loveland, Sparta, TN (US); Mario Cala, Coral Cables, FL (US); Robert Brarens, Cincinnati, OH (US)

(73) Assignee: WRIGHT MEDICAL TECHNOLOGY, INC., Memphis, TN (US)

( * ) Notice: Subject to any disclaimer, the term of this patent is extended or adjusted under 35 U.S.C. 154(b) by 321 days.

(21) Appl. No.: 17/786,078

(22) PCT Filed: Nov. 9, 2020

(86) PCT No.: PCT/US2020/059611
§ 371 (c)(1),
(2) Date: Jun. 16, 2022

(87) PCT Pub. No.: WO2021/167655
PCT Pub. Date: Aug. 26, 2021

(65) Prior Publication Data
US 2023/0025511 A1  Jan. 26, 2023

Related U.S. Application Data

(60) Provisional application No. 62/977,825, filed on Feb. 18, 2020.

(51) Int. Cl.
*A61B 17/64* (2006.01)
*A61B 17/66* (2006.01)
*A61B 17/60* (2006.01)

(52) U.S. Cl.
CPC ...... *A61B 17/6483* (2013.01); *A61B 17/6475* (2013.01); *A61B 17/66* (2013.01); *A61B 2017/606* (2013.01)

(58) Field of Classification Search
CPC ............ A61B 17/6483; A61B 17/6416; A61B 17/6466; A61B 17/6475; A61B 17/66
See application file for complete search history.

(56) References Cited

U.S. PATENT DOCUMENTS

| | | |
|---|---|---|
| 1,160,451 A | 11/1915 | Sanford |
| 3,159,074 A | 12/1964 | Neuschotz |

(Continued)

FOREIGN PATENT DOCUMENTS

| | | | |
|---|---|---|---|
| BR | 8807680 A | 8/1990 | |
| JP | H09215699 A | * 8/1997 | ........... A61B 17/663 |

(Continued)

OTHER PUBLICATIONS

International Search Report and Written Opinion issued in connection with International Patent Application No. PCT/US2020/059611, Feb. 4, 2021, 12 pages.

(Continued)

*Primary Examiner* — Julianna N Harvey
(74) *Attorney, Agent, or Firm* — DUANE MORRIS LLP

(57) ABSTRACT

An orthopedic device is disclosed that includes a threaded elongated shaft having a length, a regular polygon cross-section, and a longitudinal axis defined therethrough, wherein the elongated shaft having side surfaces extending over the length of the elongated shaft wherein each side surface corresponds to each of the sides of the regular polygon cross-section; and a pair of clamps releasably clamped on to the threaded elongated shaft, wherein each of the clamps is configured for holding up to two bone fixation (Continued)

pins in an orientation that is non-parallel with the longitudinal axis of the elongated shaft.

15 Claims, 14 Drawing Sheets

(56) References Cited

U.S. PATENT DOCUMENTS

| | | | |
|---|---|---|---|
| 4,575,035 A | 3/1986 | McDonough | |
| 4,978,348 A | 12/1990 | Ilizarov | |
| 6,716,212 B1 | 4/2004 | Pickens | |
| 6,942,664 B1* | 9/2005 | Voor | A61B 17/645 |
| | | | 606/54 |
| 2005/0043731 A1* | 2/2005 | Labbe | A61B 17/663 |
| | | | 606/57 |
| 2007/0198012 A1* | 8/2007 | Thomke | F16B 7/0493 |
| | | | 606/54 |
| 2009/0054897 A1* | 2/2009 | Gordon | A61B 17/66 |
| | | | 606/57 |
| 2014/0276818 A1* | 9/2014 | Wong | A61B 17/645 |
| | | | 606/56 |
| 2017/0281234 A1 | 10/2017 | Muniz et al. | |

FOREIGN PATENT DOCUMENTS

| | | |
|---|---|---|
| WO | 2005120403 A2 | 12/2005 |
| WO | 2008010779 A2 | 1/2008 |
| WO | 2011121512 A2 | 10/2011 |

OTHER PUBLICATIONS

Extended European Search Report issued in connection with corresponding European Patent Application No. 20920097.1, Nov. 15, 2023, 8 pages.

* cited by examiner

BONE FIXATION DEVICE

CROSS-REFERENCE TO RELATED APPLICATIONS

This application is a National Stage Application, filed under 35 U.S.C. 371, of International Patent Application No. PCT/US2020/059611, filed on Nov. 9, 2020, which claims priority to U.S. Provisional Patent Application No. 62/977,825, filed on Feb. 18, 2020, the entireties of which are is incorporated herein by reference.

FIELD OF DISCLOSURE

The present disclosure relates to the field of orthopedics and more particularly to an external orthopedic device for providing fixation, reduction, or distraction of bone segments.

BACKGROUND

External orthopedic devices are used in many orthopedic treatments to fixate, distract, compress, or reduce bone segments. Generally, fixation devices or fixators are used to stabilize bone pieces and to facilitate the healing of bones at a bone repair site. Such fixators can be used by orthopedic surgeons to restore the patient's anatomy at a fracture following an injury or distract an osteotomy site in bone lengthening procedures. During the initial installation of the fixation device to the patient, the robustness and simplicity of the fixation device in its ability to accommodate adjusting the distances between the bone fixation pins and adjusting the approach angle of the fixation pins is desirable.

Thus, there is a continuing need for an improved external fixator that can provide such adaptability.

SUMMARY

An orthopedic device is disclosed which comprises a threaded elongated shaft and one or more clamps configured to be releasably clamped on to the threaded elongated shaft. The threaded elongated shaft comprises: a length; a longitudinal axis defined therethrough; and one or more flat side surfaces extending over at least a portion of the length of the elongated shaft; and when clamped on to the threaded elongated shaft, each of the clamps is configured for holding at least one bone fixation pin in an orientation that is non-parallel with the longitudinal axis of the elongated shaft and parallel to the one or more flat side surfaces of the elongated shaft. Each of the one or more clamps is configured to be selectively rotated about the longitudinal axis of the elongated shaft, so that the bone fixation pins can be parallel to a selected one of the at least two flat surfaces of the elongated shaft, where each clamp comprises: a main body portion; a clamping piece, where the main body portion and the clamping piece form a channel that is sized for receiving the threaded elongated shaft and releasably clamping on to the elongated shaft. A threaded nut is provided at one end of the channel and rotatably engage the main body, where the threaded nut is configured for threadably engaging the elongated shaft when the elongated shaft is clamped within the channel.

In a further embodiment, a clamp is provided that is configured to be releasably coupled onto a threaded elongated shaft. The clamp may include a main body portion together with a spring-loaded clamping piece form a channel that is sized for receiving the threaded elongated shaft and releasably clamping onto the elongated shaft. A threaded nut is often provided at one end of the channel so as to rotatably engage the main body so that the threaded nut may be configured for threadably engaging the elongated shaft when the elongated shaft is clamped within the channel. Often, when clamped on to the threaded elongated shaft, the clamp is configured to hold at least one bone fixation pin in an orientation that is non-parallel with the longitudinal axis of the elongated shaft. Additionally, the clamp may be configured to selectively rotate about the longitudinal axis of the elongated shaft. Often, the threaded nut includes two portions that are hinged together to split open for receiving the threaded elongated shaft. One of the two portions of the threaded nut are internally threaded such that when the two portions are closed around the threaded elongated shaft, the threads provide on one of the two portion engaging with the threads on the elongated threaded shaft.

BRIEF DESCRIPTION OF THE DRAWINGS

The inventive concepts of the present disclosure will be described in more detail in conjunction with the following drawing figures. The structures in the drawing figures are illustrated schematically and are not intended to show actual dimensions.

FIG. 6B is a cross-section view of the clamp member taken through the section line A-A shown in FIG. 6A.

FIG. 8F is a sectional view of the threaded nut taken through the section line A-A in FIG. 8A.

FIG. 9F is a sectional view of the threaded nut taken through the section line A-A in FIG. 9A.

DETAILED DESCRIPTION

Figure 1:
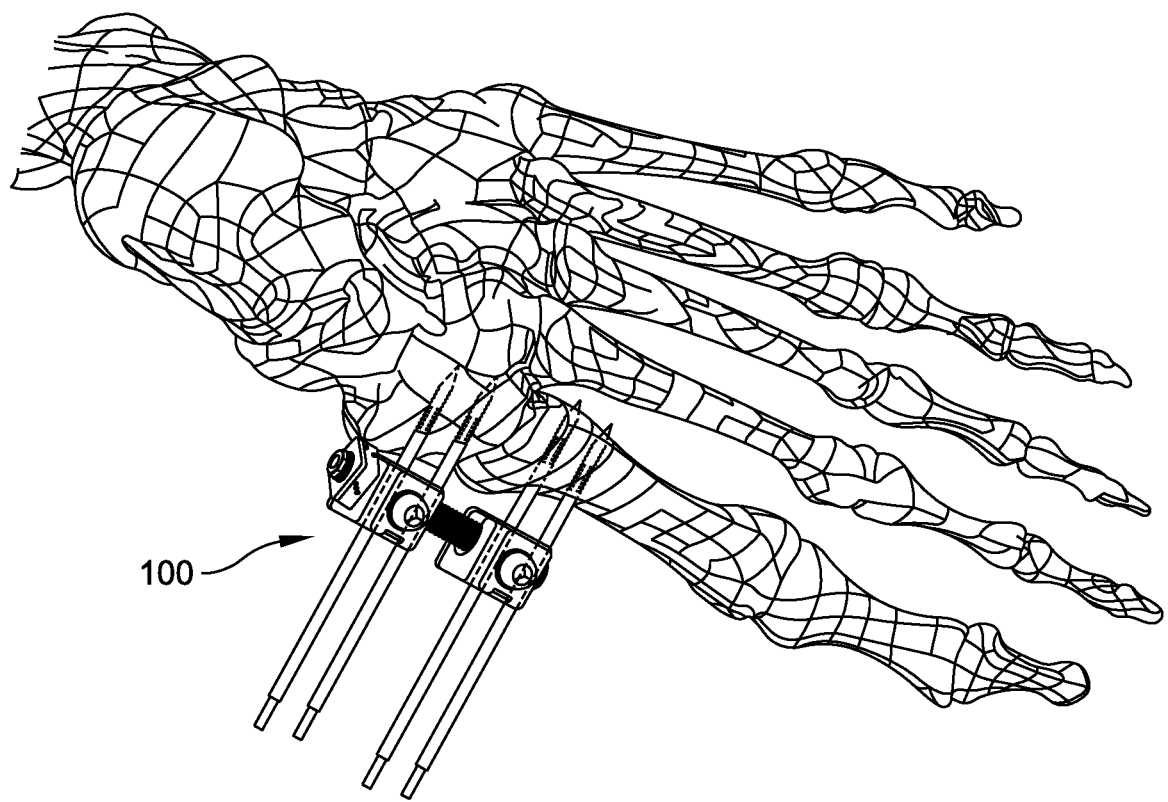
FIG. 1 is an illustration of a human foot bone and a bone fixation device of the present disclosure.

This description of the exemplary embodiments is intended to be read in connection with the accompanying drawings, which are to be considered part of the entire written description. The drawing figures are not necessarily to scale and certain features may be shown exaggerated in scale or in somewhat schematic form in the interest of clarity and conciseness. In the description, relative terms such as "horizontal," "vertical," "up," "down," "top" and "bottom" as well as derivatives thereof (e.g., "horizontally," "downwardly," "upwardly," etc.) should be construed to refer to the orientation as then described or as shown in the drawing figure under discussion. These relative terms are for convenience of description and normally are not intended to require a particular orientation. Terms including "inwardly" versus "outwardly," "longitudinal" versus "lateral" and the like are to be interpreted relative to one another or relative to an axis of elongation, or an axis or center of rotation, as appropriate. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise. When only a single machine is illustrated, the term "machine" shall also be taken to include any collection of machines that individually or jointly execute a set (or multiple sets) of instructions to perform any one or more of the methodologies discussed herein. The term "operatively connected" is such an attachment, coupling or connection that allows the pertinent structures to operate as intended by virtue of that relationship. In the claims, means-plus-function clauses, if used, are intended to cover the structures described, suggested, or rendered obvious by the written description or drawings for performing the recited function, including not only structural equivalents but also equivalent structures.

Unless otherwise expressly stated, it is in no way intended that any method set forth herein be construed as requiring that its steps be performed in a specific order, nor that with any apparatus, specific orientations be required, unless specified as such. Accordingly, where a method claim does not actually recite an order to be followed by its steps, or that any apparatus claim does not actually recite an order or orientation to individual components, or it is not otherwise specifically stated in the claims or description that the steps are to be limited to a specific order, or that a specific order or orientation to components of an apparatus is not recited, it is in no way intended that an order or orientation be inferred, in any respect. This holds for any possible non-express basis for interpretation, including: matters of logic with respect to arrangement of steps, operational flow, order of components, or orientation of components; plain meaning derived from grammatical organization or punctuation, and; the number or type of embodiments described in the specification.

Referring to FIGS. 1 through 12C, an orthopedic device assembly 100 useful for compression and distraction of bones according to some embodiments is disclosed. The orthopedic device assembly 100 comprises a threaded elongated shaft 170, one or more clamps 110 that are configured to be releasably clamped on to the threaded elongated shaft 170. The threaded elongated shaft 170 has a length L, a longitudinal axis A defined therethrough, and one or more flat side surfaces S extending over at least a portion of the length L of the elongated shaft 170. All or a portion of the exterior of the elongated shaft 170 comprises threads 175.

Figure 9C:
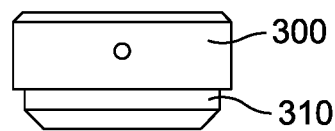
FIGS. 9A-9F are illustrations showing different views of monolithic compression/distraction nut of the bone fixation device.
Figure 9D:
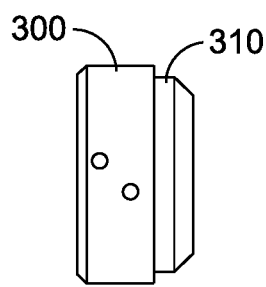
Figure 9A:
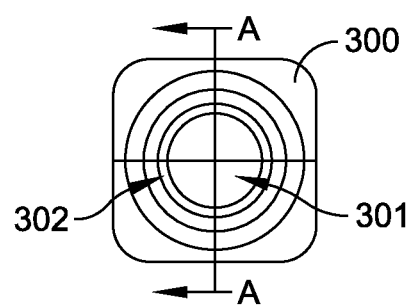
Figure 9B:
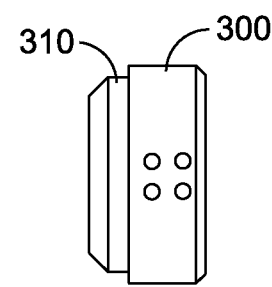
Figure 9E:
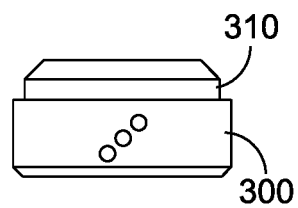
Figure 9F:
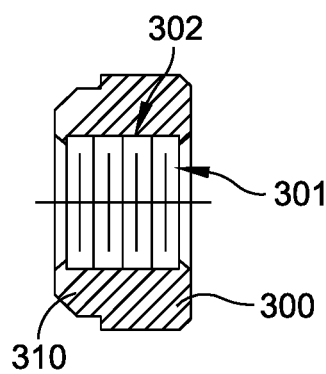

It should be noted that the side surfaces S are being refer to as flat surfaces but they are not flat planar surfaces. They are referred to as being flat because when a lateral cross-section is taken of the threaded elongated shaft 170, the cross section is not a circle but has flat sides S as shown in FIG. 9B. The flat sides S cannot be planar because of the threads 175 on the outer surface of the elongated shaft 170. The end view 170A of the threaded elongated shaft 170 shown in FIG. 9A is also illustrative.

Figure 2A:
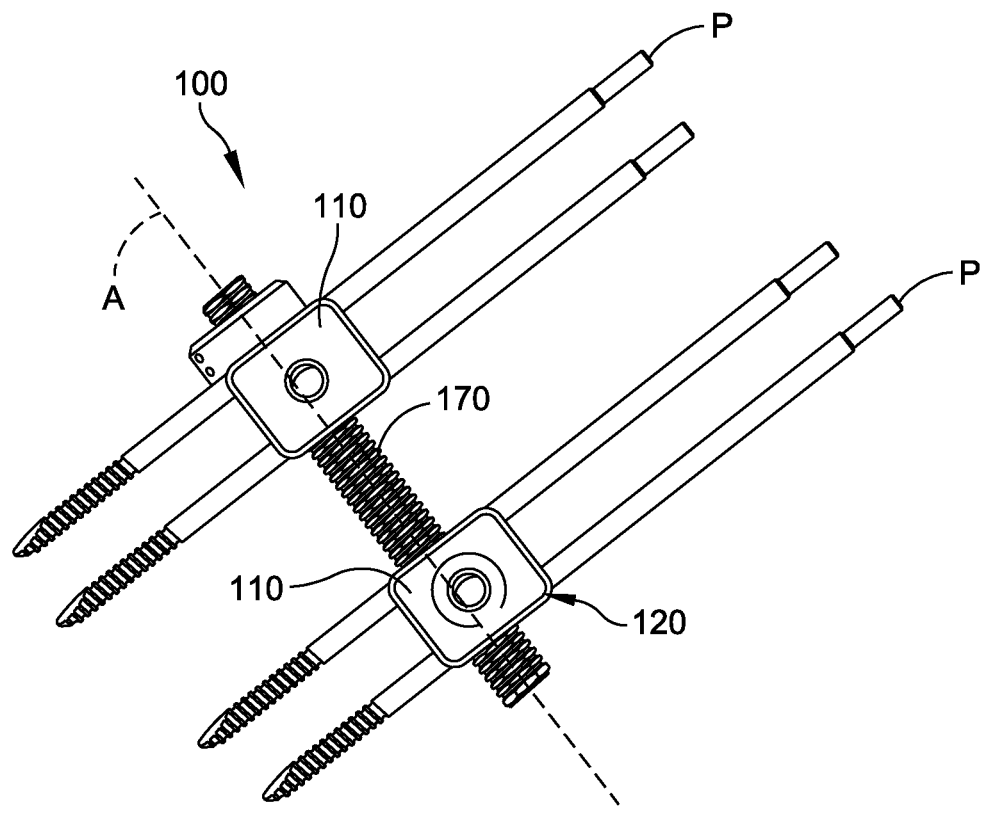
FIG. 2A is an illustration of the bone fixation device of the present disclosure according to an embodiment.

Referring to FIG. 2A, when clamped on to the threaded elongated shaft 170, each of the one or more clamps 110 is configured for holding at least one bone fixation pin P. Preferably, the clamps 110 hold at least one bone fixation pin P in an orientation that is non-parallel with the longitudinal axis A of the elongated shaft and parallel to one of the one or more flat side surfaces S of the elongated shaft. Each clamp is configured to be selectively rotated about the longitudinal axis A of the threaded elongated shaft 170, so that in embodiments where there are more than one flat side surfaces S, the bone fixation pins are parallel to a different one of the flat side surfaces S of the threaded elongated shaft 170. Each of the clamps 110 comprises a main body portion 112, and a clamping piece 114 for selectively and releasably clamping onto the threaded elongated shaft 170. The main body portion 112 and the clamping piece 114 form a channel C that is sized for receiving the threaded elongated shaft 170 and releasably clamping on to the elongated shaft.

Figure 2B:
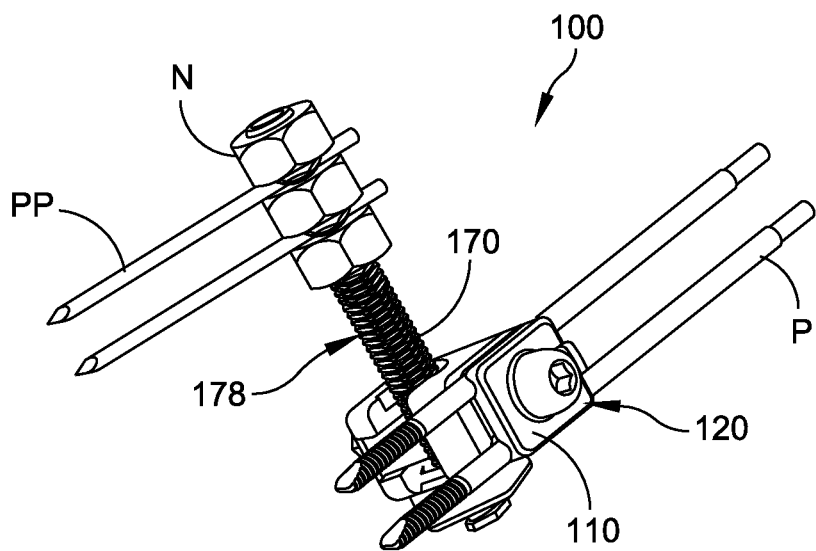
FIG. 2B is an illustration of the bone fixation device of the present disclosure according to another embodiment.

Referring to FIG. 2B, in some embodiments, the orthopedic device assembly 100 can be configured with one clamp member 110. In this embodiment, the elongated shaft 170 comprises a plurality of holes 178 located at various select points along the length of the elongated shaft 170 in one or more of the flat side surfaces S. The provision of the plurality of holes 178 can be seen more clearly in FIGS. 3J-3K. The holes 178 in the elongated shaft 170 are intended for receiving a first set of fixation wires/pins PP and the holes 178 extend through the elongated shaft 170 perpendicular to the longitudinal axis A of the elongated shaft 170. The first set of fixation wires/pins PP can be secured to the elongated shaft 170 using double nuts N for each wire. Thus, one end of the elongated shaft 170 can be attached to a first bone piece using the first set of fixation wires/pins PP and a second set of fixation wires/pins P held by the clamp member 110 can be used to attach the second end of the elongated shaft 170 to a second bone piece. FIG. 3L is a cross-sectional view of the elongated shaft 170 through the section line A-A shown in FIG. 3K. The cross-section is taken through some of the plurality of holes 178.

Referring back to FIG. 2B, with the embodiment of the elongated shaft 170 having the plurality of holes 178, one or more fixation pins such as a half pin PP can be inserted through the holes 178 and locked in place using threaded nuts N. One end of the fixation assembly 100 then can be secured to a first location on the bone being treated using the half pins PP. Next, one clamp member 110 is clamped on to the other end of the elongated shaft 170 as shown. The bone fixation pins P can be secured to a second location on the bone being treated. These bone fixation pins P are held by the clamp member 110 via operation of the pin cover 120. The detailed structure of the clamp member 110 will be described below.

Figure 3A:
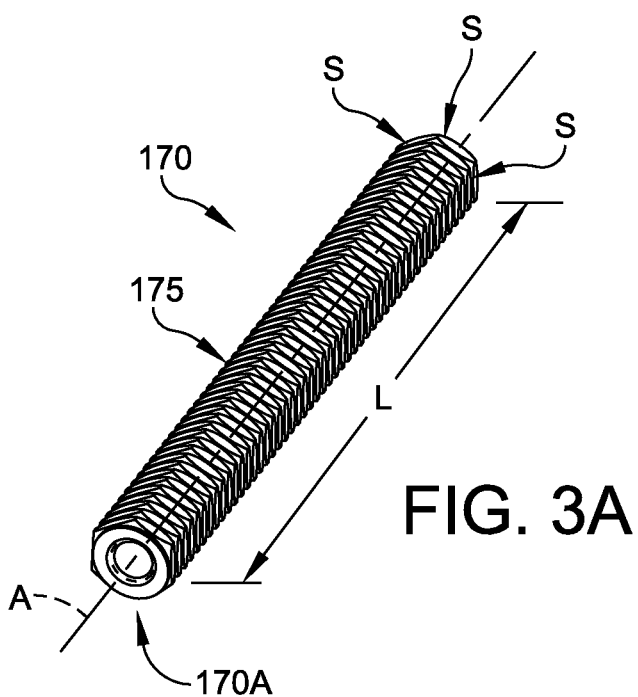
FIG. 3A is an isometric view illustration of an embodiment of the threaded elongated shaft of the bone fixation device.
Figure 3B:
FIG. 3B is an end view of the threaded elongated shaft of FIG. 3A.
Figure 3C:
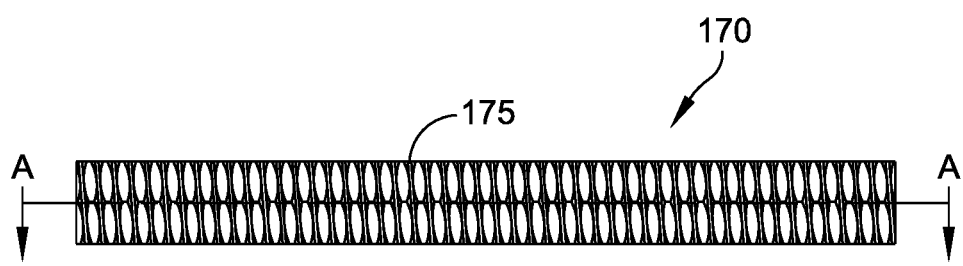
FIG. 3C is an elevation view illustration of the threaded elongated shaft of FIG. 3A.
Figure 3D:
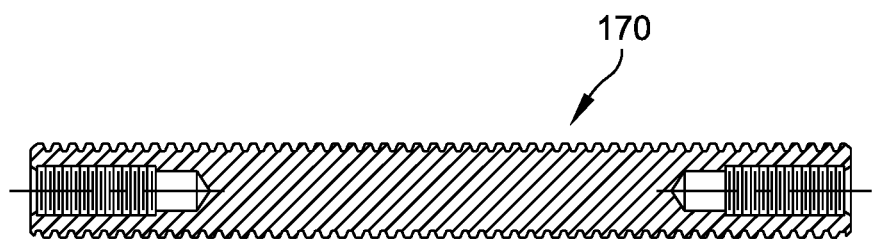
FIG. 3D is a longitudinal cross-sectional view of the threaded elongated shaft taken through the section line A-A shown in FIG. 3C.
Figure 3E:
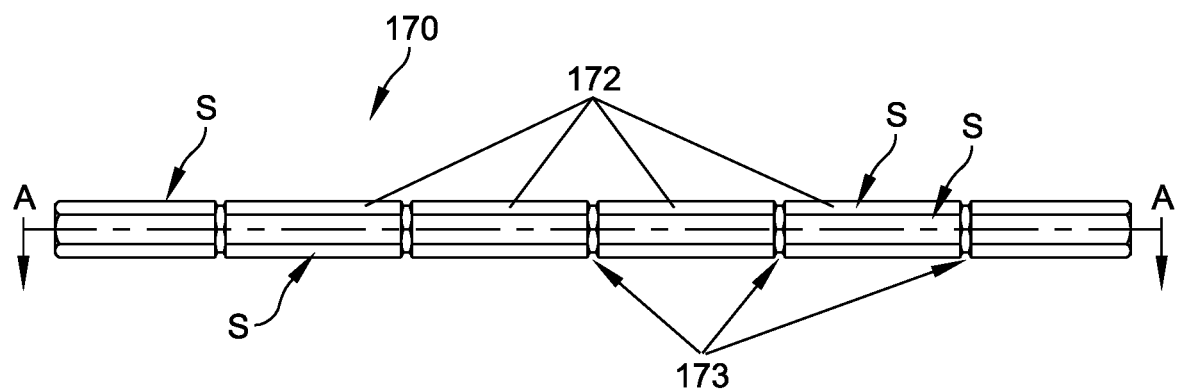
FIG. 3E is an elevation view illustration of another embodiment of the threaded elongated shaft of the bone fixation device.
Figure 3F:
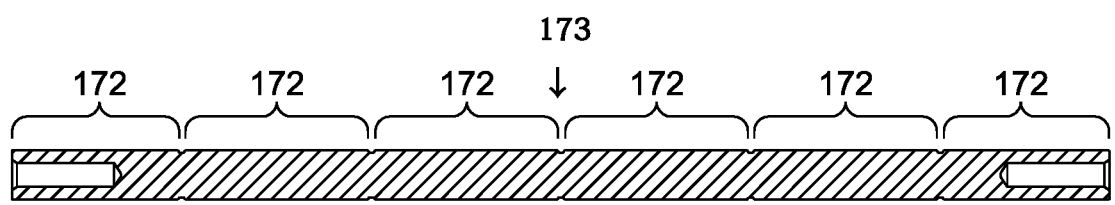
FIG. 3F is a longitudinal cross-sectional view of the threaded elongated shaft taken through the section line A-A shown in FIG. 3E.
Figure 3G:
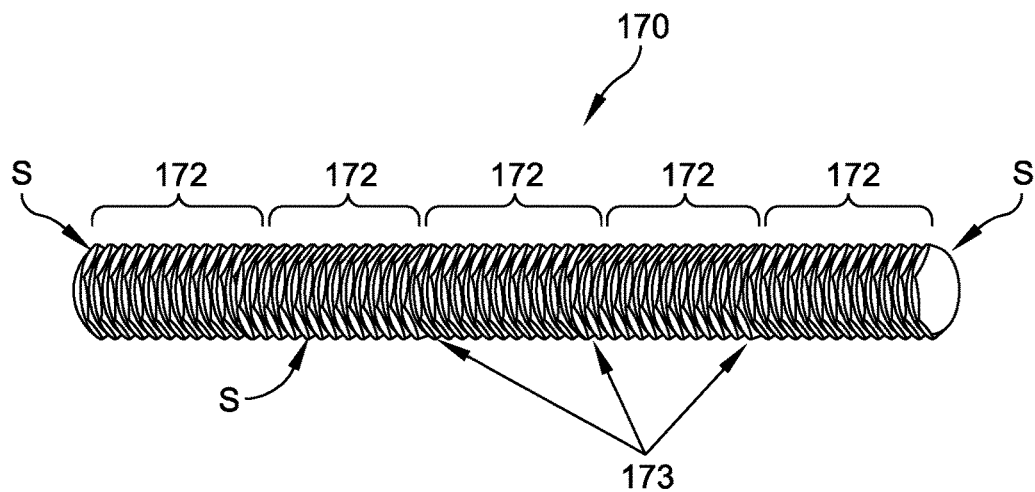
FIG. 3G is an isometric view illustration of another embodiment of the threaded elongated shaft of the bone fixation device.
Figure 3H:
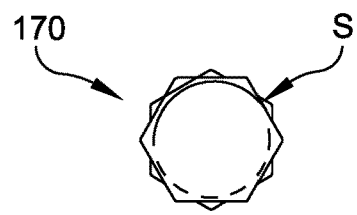
FIG. 3H is an end view of the threaded elongated shaft of FIG. 3G.
Figure 3I:
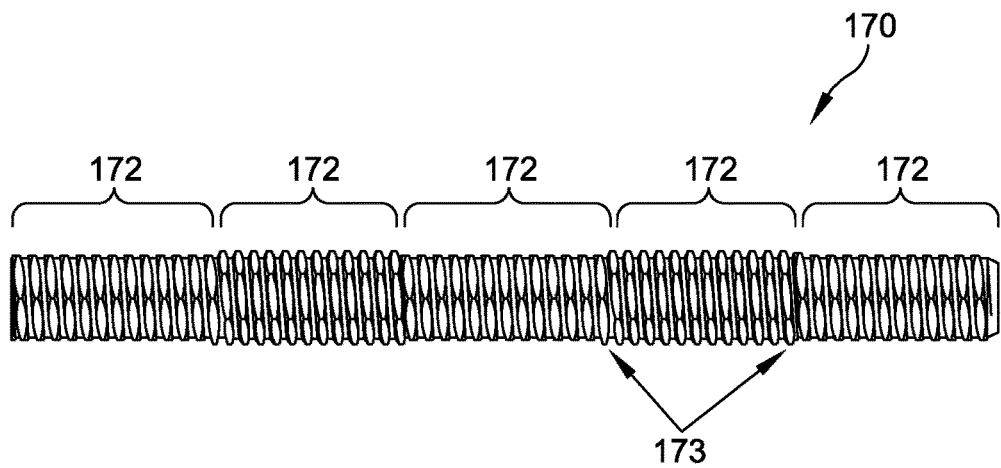
FIG. 3I is an elevation view of the threaded elongated shaft of FIG. 3G.
Figure 3J:
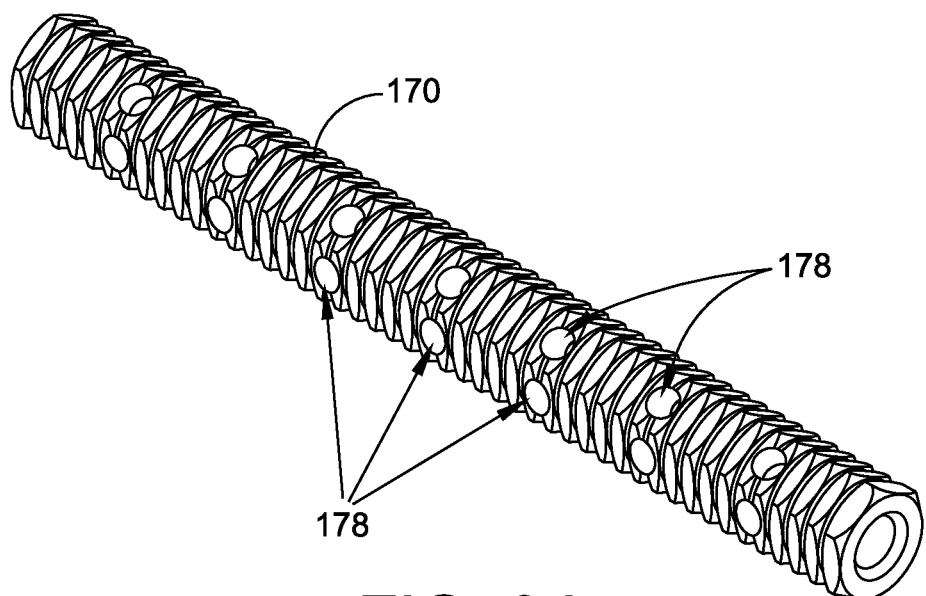
FIG. 3J is an isometric view illustration of another embodiment of the threaded elongated shaft of the bone fixation device.
Figure 3K:
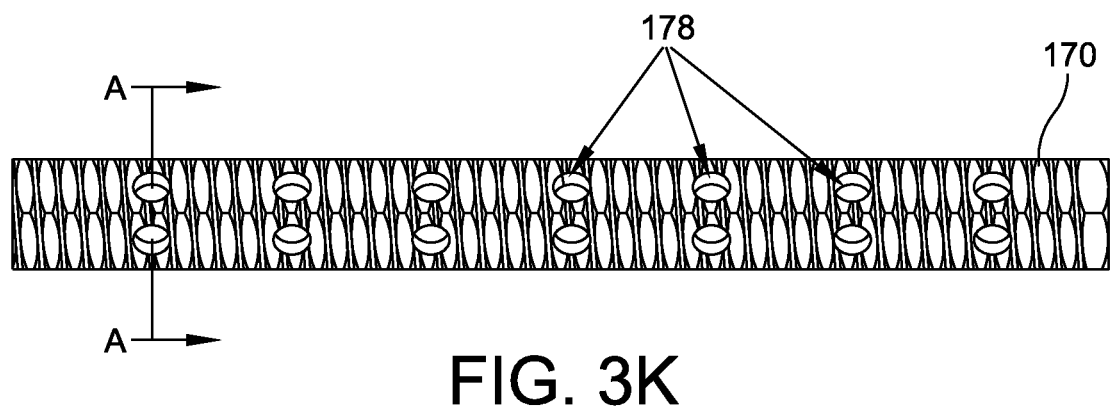
FIG. 3K is an elevation view of the threaded elongated shaft of FIG. 3J.
Figure 3L:
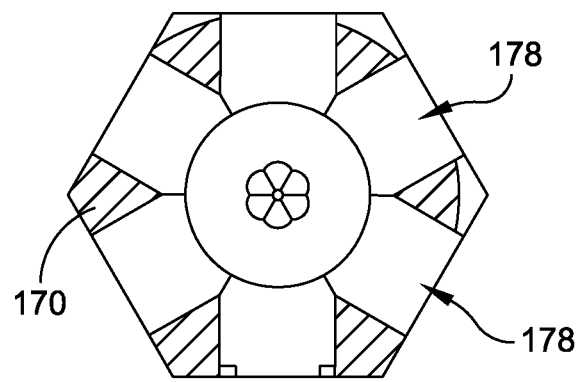
FIG. 3L is a cross-sectional view of the threaded elongated shaft of FIG. 3K taken through the section line A-A shown in FIG. 3K.

Referring to FIGS. 3E-3I, in some embodiments of the assembly 100, the elongated shaft 170 comprises two or more portions 172 over the length of which the one or more flat side surfaces S extend. Each of the two or more portions 172 can be separated by a gap or a groove 173. The one or more flat side surfaces S in each of the two or more portions 172 can have the same orientation or different orientation as long as the threads on the elongated shaft 170 are continuous. For example, in an embodiment of the elongated shaft 170 illustrated in FIG. 3G, each of the five portions 172 can have one or more flat side surface S and the flat side surfaces S on each of the five portions 172 can have different orientation so that the flat surfaces are facing different directions. In the particular example shown in FIG. 3G, each of the five portions 172 has six flat side surfaces S. The six flat side surfaces S form a hexagonal cross-section. FIG. 3H shows the end view of the elongated shaft 170 showing that the flat side surfaces S are in hexagonal arrangement. FIG. 3I shows an elevation view of the elongated shaft 170 embodiment of FIG. 3G.

Figure 3M:
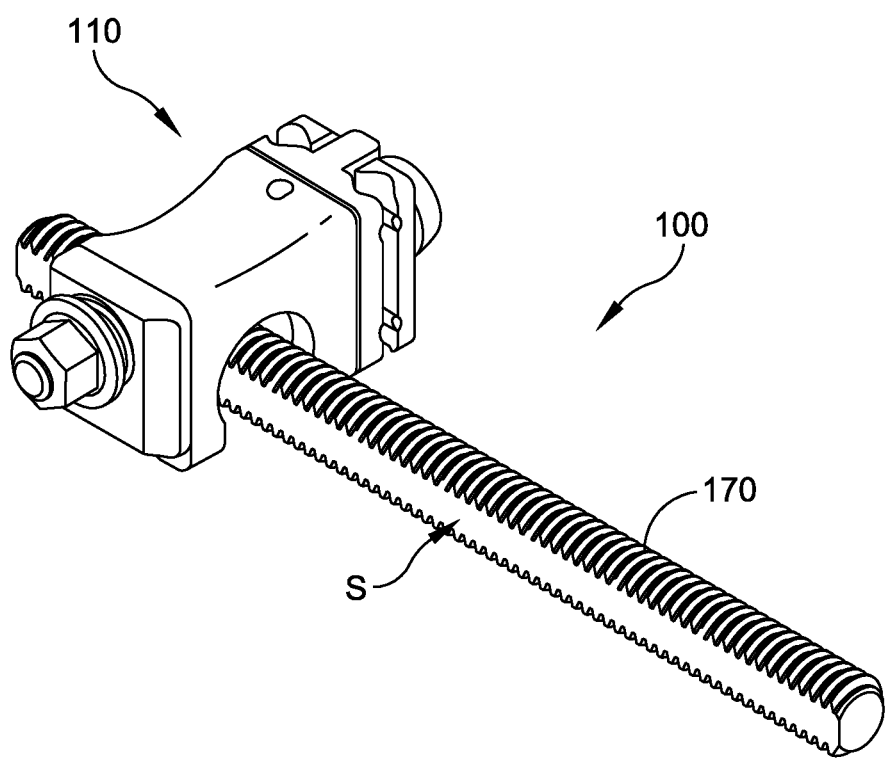
FIG. 3M is an isometric view illustration of another embodiment of the threaded elongated shaft of the bone fixation device with a clamp member engaged on it.

In some embodiments, each of the two or more portions 172 of the elongated shaft can have the same number of flat side surfaces S. In other embodiments, each of the two or more portions 172 can have different numbers of flat side surfaces S. For example, in the illustrated examples shown in FIGS. 3E-3G, each of the two or more portions 172 has six flat side surfaces S. However, in some embodiments, each of the two or more portions 172 can have a different number of flat surfaces S as long as there is at least one flat surface S. As shown in FIG. 3M the elongated shaft 170 can have just one flat surface S along the full length of the elongated shaft 170. The flat side surfaces S allow the channel C of the clamp member 110 formed by the main body portion 112 and the spring-loaded clamping piece 114 to engage the elongated shaft and hold the clamp member 110 at a selected orientation. Each selectable orientation is determined by the flat surfaces S and the number of selectable orientation is determined by the number of the flat surfaces S available in a full rotation about the longitudinal axis A. In the illustrated example, where there are six flat surfaces S in a full rotation about the longitudinal axis A, there are six selectable orientations for the clamp member 110.

In some embodiments of the assembly 100, each of the two or more portions 172 of the elongated shaft 170 can have different number of flat side surfaces. As mentioned above, the flat side surfaces on each of the two or more portions 172 can have different orientations.

In some embodiments of the assembly 100, the one or more flat side surfaces S comprises six flat surfaces. In other embodiments, the at least two flat surfaces S can comprise any desired number, e.g., 3, 4, 5, etc.

Figure 4:
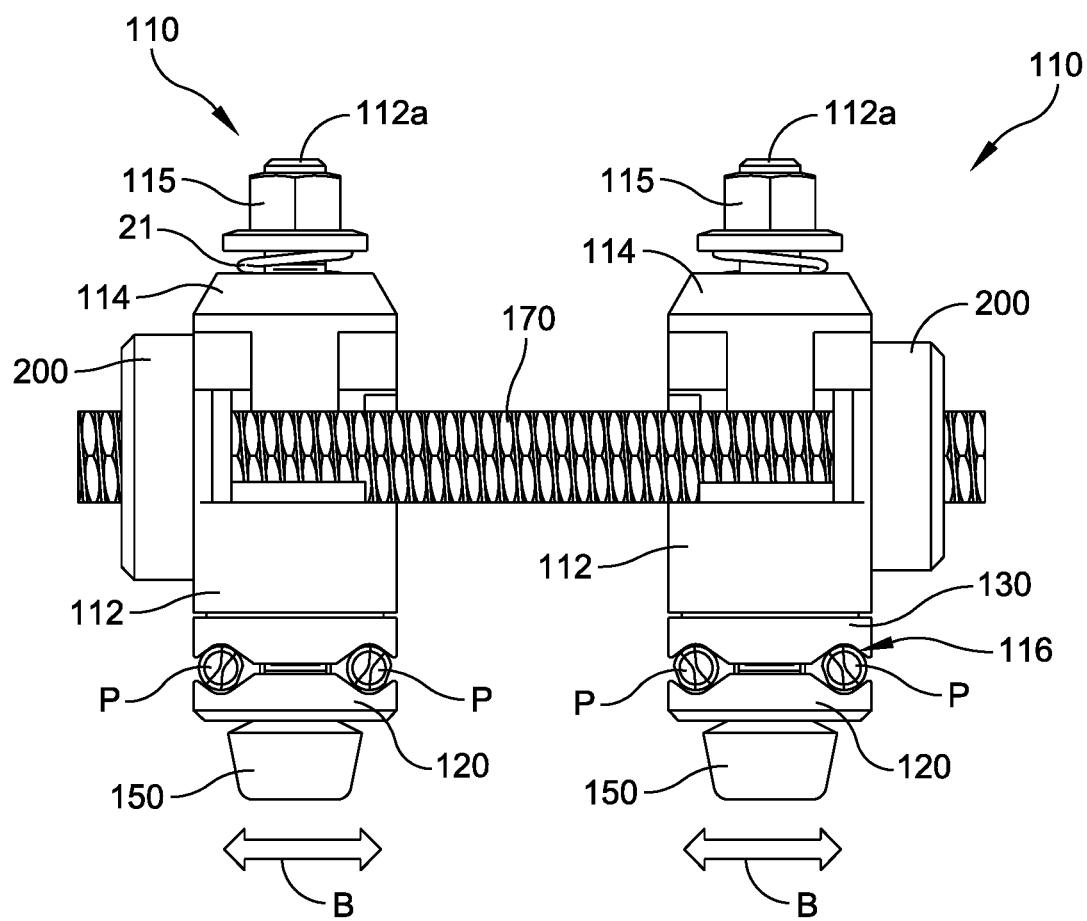
FIG. 4 is an illustration of the bone fixation device according to an embodiment.

In FIG. 4, an embodiment of the orthopedic device assembly 100 is shown that comprises two clamps 110 clamped onto the elongated shaft 170. The orthopedic device assembly 100 also includes a threaded compression/distraction ("C/D") nut 200 configured to engage a clamp member 110 at one end of the channel C (see FIG. 5A) and rotatably engages the main body 112 of the clamp member 110. The clamp member 110 is provided with a countersink 112b at one end of the channel C and the threaded C/D nut 200 is provided with an extended collar 210 (see FIGS. 8A-8E) that rotatably engages the countersink 112b. The extended collar 210 and the countersink 112b are not mechanically linked, the extended collar 210 simply fits inside the countersink 112b and allows the threaded C/D nut 200 to be rotated. The threaded C/D nut 200 is configured for threadably engaging the elongated shaft 170 when the elongated shaft is clamped within the channel C. Because the threaded C/D nut 200 is threaded on to the elongated shaft 170, by turning the threaded C/D nut 200 on one or both of the two clamps 110, the spacing between the two clamps can be adjusted to perform distraction or compression. By turning the threaded C/D nut 200 in one direction, the threaded C/D nut 200 can be moved toward the other clamp pushing the clamp that is engaging the threaded C/D nut 200 in the same direction, thus, reducing the spacing between the two clamps 110. Thus, this configuration can be used for compression application. By turning the threaded C/D nut 200 in the opposite direction, the threaded C/D nut 200 will move away from the other clamp member 110 and allow the clamp that is engaging the threaded C/D nut 200 to be pushed away from the other clamp, thus, increasing the spacing between the two clamps and relieving the compression force. These motions are noted by the arrows B in FIG. 4.

In this embodiment, the threaded C/D nut 200 is not mechanically linked to the main body 112 of the clamp member 110 and the threaded C/D nut 200 can only push against a clamp member 110. Therefore, in order to perform a distraction, the arrangement of the two clamps 110 and the associated C/D nut 200 shown in FIG. 4 needs to be swapped so that the two threaded C/D nuts 200 are on the inner sides of the two clamp members 110. In this distraction mode arrangement, the two clamp members 110 can be pushed outward by turning the threaded C/D nuts 200 to perform distraction.

Figure 5A:
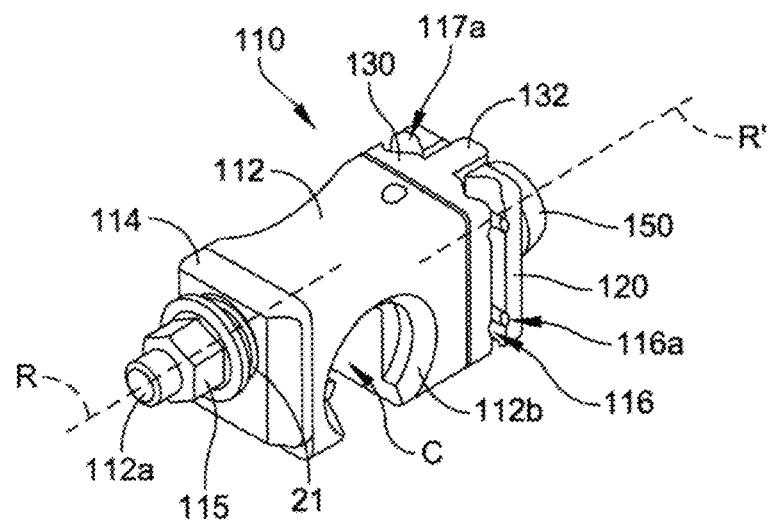
FIG. 5A is an isometric view of the clamp member of the bone fixation device according to an embodiment.
Figure 6A:
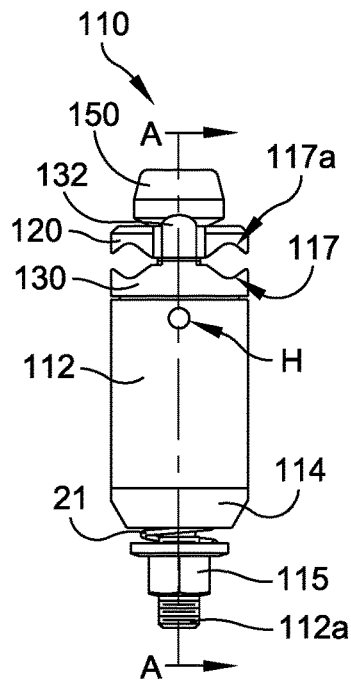
FIGS. 6A-6C are illustrations showing different views of a clamp member according to some embodiments.
Figure 6B:
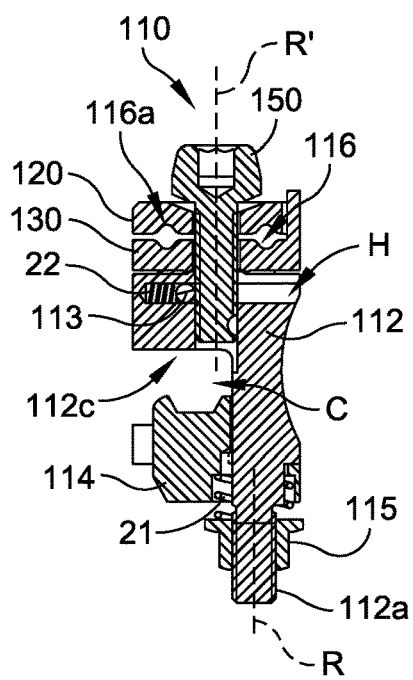
Figure 6C:
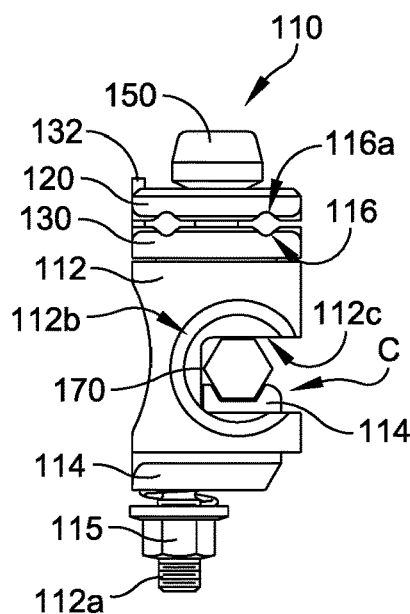

In some embodiments of the assembly 100, the main body portion 112 and the spring-loaded clamping piece 114 of the clamp member 110 are configured to conformably engage the profile of the elongated shaft 170. This can be illustrated using an example of clamp member 110 shown in FIGS. 5A, and 6A through 6C which are illustrations of an embodiment of a clamp member 110. FIG. 6A shows a view of the clamp member 110 on the side opposite from the side where the channel C is. FIG. 6B is a sectional view of the clamp member 110 taken through the section line A-A shown in FIG. 6A. FIG. 6C is a side view of the clamp member 110 (i.e., a view taken 90 degrees from the view of FIG. 6A) looking straight into the channel C. The outline of the cross-section of the elongated shaft 170, a hexagon in this example, is shown with a dashed line. In some embodiments, as illustrated in FIG. 6C, the spring-loaded clamping piece 114 and the surface 112c of the main body portion 112 are configured to conform to the hexagonal cross-section shape of the elongated shaft 170. Both the surface 112c of the main body portion 112 and the end of the spring-loaded clamping piece 114 that engage the elongated shaft 170 is shaped to conform to the contour of the elongated shaft 170. In FIG. 6C, both the surface 112c and the spring-loaded clamping piece 114 are flat matching the flat surfaces S of the hexagonal cross-section shape of the elongated shaft 170.

Figure 6D:
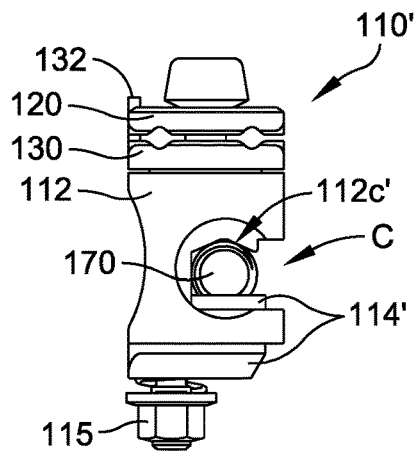
FIG. 6D is an illustration of another embodiment of the clamp member.
Figure 6E:
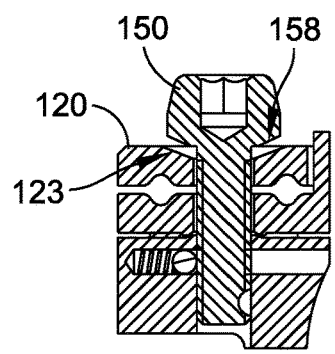
FIG. 6E is a partial cross-sectional view of a portion of the clamp member of FIGS. 6A-6D.

Referring to FIG. 6D, in some embodiments of the clamp member 110', the surface 112c' of the main body portion 112' and the clamping piece 114' do not necessarily fully conform to the shape of the elongated shaft 170. The surface 112c' can be configured to have a concave shape as shown which will be more robust in terms of engaging the threaded elongated shaft 170 having different cross-sectional shapes. In this illustrated example, the version of the threaded elongated shaft 170 is the one shown in FIG. 3M that has one flat side S that runs the full length of the elongated shaft 170. The surface of the clamping piece 114' that contacts the flat side S of the threaded elongated shaft 170 is flat. However, the surface of the clamping piece 114' that contacts the flat side S of the threaded elongated shaft 170 can be convex. When paired up in conjunction with the surface 112c' that is concave, the convex surface of the clamping piece 114' that contacts the flat side S of the threaded elongated shaft 170 works well in maintaining the rotational position of the clamp member 110' and preventing the clamp member 110' from rotating around the threaded elongated shaft 170.

As shown in FIG. 6B, the main body portion 112 of the clamp member 110 comprises a threaded screw portion 112a. In this embodiment, the clamping piece 114 is in spring-loaded configuration. The clamping piece 114 is slipped over the threaded screw portion 112a and a threaded nut 115 is threaded onto the threaded screw portion 112a and captures a coil spring 21 between the threaded nut 115 and the clamping piece 114. The coil spring 21 urges on the clamping piece 114 so that the main body portion 112 and the clamping piece 114 clamps the elongated shaft 170 in the channel C formed between them. The force exerted on the clamping piece 114 by the coil spring 21 can be adjusted by tightening or loosening the threaded nut 115. When the force exerted by the coil spring 21 is optimally adjusted, the clamp member 110 can be rotated about the elongated shaft 170 even while the clamp member 110 is securely clamped onto the elongated shaft 170. In the illustrated example, the elongated shaft 170 has a polygonal (hexagon to be exact) cross section. Thus, by applying sufficient force to turn the clamp member 110, the force will enable the clamping piece 114 to retract against the force exerted by the coil spring 21 and slide over a vertex of the polygonal cross-section of the elongated shaft 170. This allows easy adjustment to the approach angle of the bone fixation pins held by the clamp. Alternatively, the threaded nut 115 can be tightened to push the clamping piece 114 all the way and contact the elongated shaft 170 and frictionally lock on to the elongated shaft 170 so that the clamp member 110 cannot slide along the elongated shaft 170. In some embodiments, threaded screw portion 112a can be provided with a deformed threads at the bottom end (i.e., away from the clamping piece 114 and the threaded nut 115 can be backed out all the way until the nut is stopped by the deformed thread and keep the nut 115 in that position. The length of the threaded screw portion 112a is set to such a length so that when the nut 115 bottoms out, the channel C can be temporarily opened large enough to allow the elongated shaft 170 to be received into the channel C but the coil spring 21 will keep the clamping piece 114 urged against a flat side S of the elongated shaft 170 and keep the clamp member 110 from rotating around the elongated shaft 170. By selecting a coil spring 21 having an appropriate spring force one can also configure the clamp member 110 to be able to slide along the elongated shaft or prevent the clamp member 110 from sliding depending on the needs of a particular application.

The main body portion 112 of the clamp member 110 comprises a countersink 112b provided at one end of the channel C for rotatably engaging the threaded C/D nut 200. The main body portion 112 of the clamp member 110 comprises at least one groove 117 for receiving a bone fixation pin; and a pin cover plate 120 that is attached to the main body portion 112 over the at least one groove 117 for capturing a bone fixation pin P between the main body portion 112 and the pin cover plate 120. The pin cover plate 120 is attached to the main body portion 112 by a fastener such as a locking screw 150 shown in FIGS. 4, 5A, and 5E.

The locking screw 150 can be configured so that the pin cover plate 120 is non-removably captured once the clamp member 110 is assembled or the pin cover plate can be removably attached to the main body portion 112. In the illustrated examples shown in FIGS. 4, 5A, and 6A-6C, the locking screw 150 and the main body portion 112 are configured so that once the clamp member 110 is assembled, the locking screw 150 cannot be removed and permanently captures the pin cover plate 120 between the locking screw's head and the main body portion 112.

The embodiment in which the pin cover plate 120 is non-removably captured will now be described. The locking screw 150 has a threaded shaft but the threads are not shown in the illustration in FIG. 5E. As shown in the cross-sectional view of the clamp member 110 in FIG. 6B, the locking screw 150 extends through the pin cover plate 120 and the pin base plate 130 via the holes 140 and is threaded into the main body portion 112 to fasten the pin cover plate 120 and the pin base plate 130 to the main body portion 112. The head of the locking screw 150 is larger than the holes 140 so that the head of the locking screw retains the pin cover plate 120 and the pin base plate 130 against the main body portion 112.

Figure 5B:
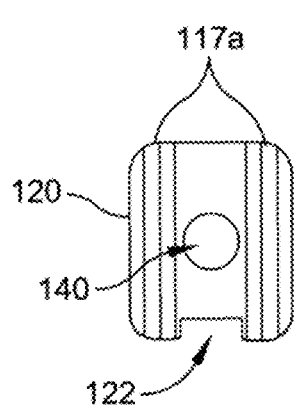
FIGS. 5B and 5D are illustrations showing examples of different embodiments for different configurations for fixation pin capturing grooves on the pin cover plate or the pin base plate.
Figure 5C:
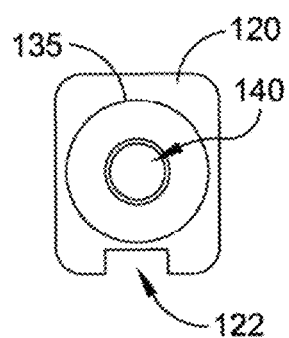
FIG. 5C is an illustration showing a bottom face of the pin base plate according to some embodiments.
Figure 5D:
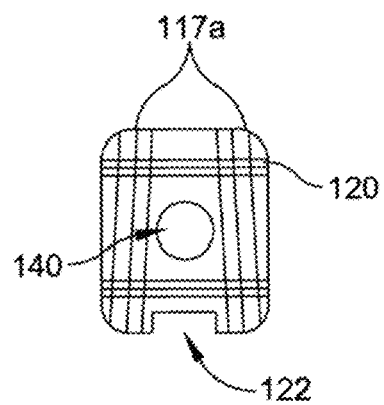
Figure 5E:
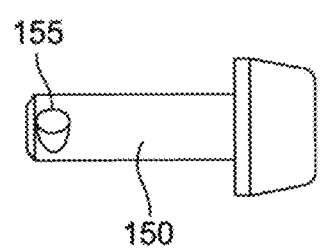
FIG. 5E is an illustration of a locking screw that fastens the pin cover plate and the pin base plate to the main body of the clamp member.

Referring to FIGS. 5E and 6B, in some embodiments, the main body portion 112 comprises retention mechanism for retaining the locking screw 150 and preventing the locking screw 150 from disengaging from the main body portion 112 (i.e., prevent the screw from falling out). The retention mechanism comprises a spring-loaded retention ball 113 that is urged against the locking screw 150 and a retention recess 155 provided on the locking screw 150. If an attempt was made to pull the locking screw 150 out from the clamp member 110 assembly, the retention ball 113 engages the retention recess 155 on the locking screw 150 and prevents the locking screw 150 from being removed. The retention ball 113 is positioned inside a hole H in the main body portion 112 and is urged against the locking screw 150. The hole H is orthogonally oriented to the locking screw 150 and intersects the locking screw 150. A coil spring 22 that is also positioned inside the hole H urges the retention ball 113 against the locking screw 150.

In some embodiments, the pin cover plate 120 comprises at least one groove 117a. Each groove 117a provided on the pin cover plate 120 corresponds to each of the at least one groove 117 provided on the main body portion 112 and is aligned with the corresponding one of the at least one groove 117 provided on the main body portion 112. FIGS. 5B and 5D are illustrations showing the possible arrangements of the at least one groove 117a on the pin cover plate 120 as well as the at least one groove 117 provided on the main body portion 112.

Pin cover plate 120 can have one or a pair of grooves 117a and the opposing surface (either directly on the main body portion 112 or on the pin base plate 130) can have the corresponding matching grooves 117.

In embodiments where two grooves 117a are provided on the pin cover plate 120 and the corresponding two grooves 117 are provided on the main body portion 112 (or the pin base plate 130), the result is that there are two pairs of aligned grooves between the pin cover plate 120 and the main body portion 112 (or the pin base plate 130). The two pairs of grooves can be parallel to each other or they can be provided in a non-parallel orientation. The example of parallel arrangement of the grooves 117a is shown in FIG. 5B. In the example shown in FIG. 5D, the grooves 117a are in non-parallel arrangement. The corresponding grooves 117 on the main body portion 112 (or the base plate 130) would be arranged to mirror the grooves 117a.

Figure 5F:
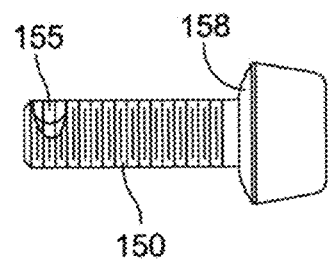
FIG. 5F is an illustration of a locking screw that fastens the pin cover plate and the pin base plate to the main body of the clamp member where the screw head has a spherical bottom surface.
Figure 5G:
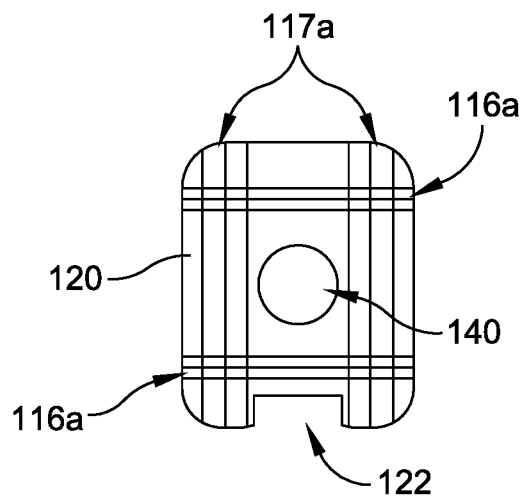
FIGS. 5G and 5H are illustrations showing additional examples of different embodiments for different configurations for fixation pin capturing grooves on the pin cover plate or the pin base plate.
Figure 5H:
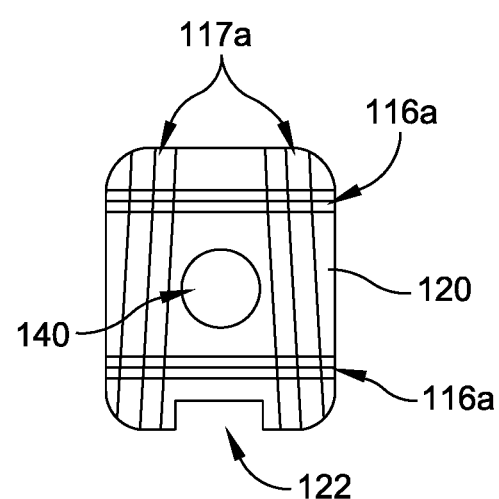

Referring to FIGS. 5G and 5H, in some embodiments, the pin cover plate 120 can be provided with a second set of grooves 116a. The second set of grooves 116a are oriented substantially orthogonal to the first set of grooves 117a. The first set of grooves 117a and the second set of grooves 116a can be of different sizes, i.e., the width and depth of the grooves can be different, to accommodate different diameter fixation pins. For example, in the examples shown in FIGS. 5G and 5H, the second set of grooves 116a can be of different size from the first set of grooves 117a. In the illustrated embodiment, the second set of grooves 116a are narrower and shallower than the first set of grooves 117a. In these embodiments, the pin base plate 130 can be provided with matching second set of grooves 116. To select between the first set 117/117a or the second set 116/116a of grooves, the pin base plate 130 and the pin cover plate 120 assembly can be rotated 90 degrees about the rotational axis R' of the locking screw 150. The rotational axis R and R' are noted in FIGS. 5A and 6B. In the examples of the clamp member 110 shown in FIGS. 5A, 6A-6C, the pin cover plate 120 is of the embodiments shown in FIGS. 5G and 5H and thus comprise two sets of grooves 117a and 116a that are oriented substantially orthogonal to each other. Thus, in the view shown in FIG. 6A, the first set of grooves 117a are visible and in the view shown in FIG. 6C in which the clamp member 110 is rotated 90 degrees, the second set of grooves 116a are visible. In this embodiment, the pin base plate 130 comprises the corresponding first and second grooves 117 and 116.

In the embodiments where the pin base plate 130 are provided, the pin base plate 130 and the pin cover plate 120 can be configured to be keyed to each other to maintain rotational alignment, in other words prevent them from rotating with respect to each other, when assembled into a clamp member 110. For example, the pin base plate 130 can be provided with an alignment tab 132 (see FIGS. 5A, 6A-6D) and the pin cover plate 120 can be provided with a recess 122 (see FIGS. 5B-5D, and 5G-5H) that mates with the alignment tab 132. The isometric view of the clamp member 110 in FIG. 5A shows the alignment tab 132 and the recess 122 keyed to each other keeping the first set of grooves 117/117a and the second set of grooves 116/116a aligned.

In some embodiments, for a given first set of grooves 117/117a or the second set of grooves 116/116a, two different diameter fixation pins can be accommodated at the same time. This is enabled by the spherical bottom surface 158 of the head of the locking screw 150 and the collar of the hole 140 having a chamfered edge 123 on the top side of the pin cover plate 120 as shown in FIG. 6B and in more detail in FIG. 6E. The chamfered hole 140 and the spherical radius of the bottom of the screw head 150 accommodates the tilting of the pin cover plate 120 when two pins having different diameters are captured between the pin cover plate 120 and the pin base plate 130, one pin in each of the pair of grooves 117/117a or 116/116a. FIG. 5F shows an embodiment of the locking screw 150 where the screw head has a spherical bottom surface 158.

Referring to FIG. 5A, in some preferred embodiments, the main body portion 112 comprises a pin base plate 130 and the at least one groove 117a in the main body portion is provided on the pin base plate 130. FIGS. 5B and 5D illustrate the arrangement of the at least one groove 117a on the pin cover plate 120. In the embodiment of the pin cover plate 120 shown in FIG. 5B, there are two grooves 117a provided in substantially parallel arrangement. In another embodiment of the pin cover plate 120 shown in FIG. 5D, the two grooves 117a are Referring to FIGS. 6A-6C, in some embodiments, the pin cover plate 120 and the pin base plate 130 are configured with two additional grooves 117a, 117, that are oriented at an angle of about 10 to 90 degrees from the grooves 116a, 116. FIG. 6B is a view of the clamp member 110 assembly at a viewing angle 90 degrees turned from the view in FIG. 6C. Each of the two additional grooves 117a, 117 are configured for receiving bone fixation pins P having substantially different diameter. Thus, each of the additional grooves 117a, 117 have different width than the grooves 116a, 116. In use, the pin cover plate 120 and pin base plate 130 are rotated to select between the first set of grooves 116a, 116 and the additional set of grooves 117a, 117 to select the grooves having the appropriate widths for the bone fixation pins P that are needed. In the illustrated example shown in FIGS. 6A-6C, the additional grooves 117a, 117 are wider grooves than the grooves 116a, 116. The additional grooves 117a, 117 can accommodate bone fixation pins P of larger diameter.

FIG. 5C shows the side of the pin cover plate 120 that contacts the head of the locking screw 150. In some embodiments, the surface of the pin cover plate 120 that contacts the head of the locking screw 150 can be configured to provide some friction between the pin cover plate 120 and the head of the locking screw 150 to prevent the locking screw 150 from loosening. In some embodiments, this can be achieved by providing circular or radial grooves 135 on the surface of the pin cover plate 120.

Each of the embodiments of the clamp members 110, and 110' discussed above in connection with FIGS. 1 through 6D are configured to hold one set of at least one bone fixation pins P between the pin cover plate 120 and the main body portion 112 (or the pin base plate 130). FIGS. 7A-7D illustrate an embodiment of a clamp member 110A which is configured to hold two sets of at least one bone fixation pins P. The clamp member 110A comprises a main body portion 112 that is configured in a similar manner to the main body portion 112 of the clamp member 110 embodiment discussed above. The main body portion 112 comprises a clamping piece 114, a threaded portion 112a, and a threaded nut 115. The clamping piece 114 and the main body portion 112 form a channel C that receives the threaded elongated shaft 170.

In this embodiment, the main body portion 112 of the clamp member 110A comprises at least one first groove 116 for receiving a bone fixation pin P; a pin cover plate 120 that is secured to the main body portion 112 and comprises at least one second groove 116a for receiving a bone fixation pin P; and an intermediate pin cover plate 125 that is sandwiched between the main body portion 112 and the pin cover plate 120, where the intermediate pin cover plate 125 has a first side 125a that faces the main body portion 112 and a second side 125b that faces the pin cover plate 120, where the first side 125a of the intermediate pin cover plate 125 comprises at least one groove 116c for receiving a bone fixation pin P between the intermediate cover plate 125 and the main body portion 112. The second side 125b of the intermediate pin cover plate 125 comprises at least one groove 116b for receiving a bone fixation pin P between the intermediate pin cover plate 125 and the pin cover plate 120. Thus, there can be two sets of bone fixation pins P held by the clamp member 110A: a first set of bone fixation pins P held by the grooves 116 and 116c between the intermediate pin cover plate 125 and the main body portion 112; and a second set of bone fixation pins P' held by the grooves 116b and 116a between the intermediate pin cover plate 125 and the pin cover plate 120.

Figure 7A:
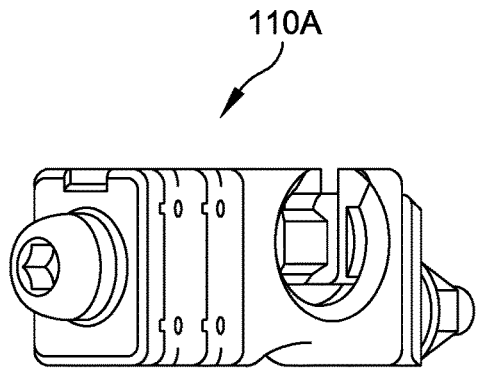
FIG. 7A is an isometric view of a clamp member according to another embodiment.
Figure 7D:
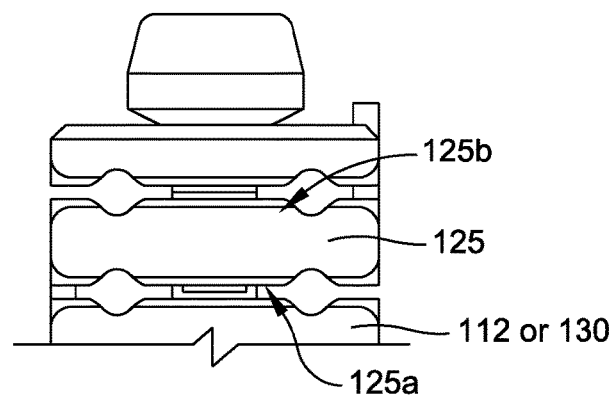
FIG. 7D is a detailed view of the intermediate pin cover plate portion of the clamp member of FIGS. 7A-7C.
Figure 7B:
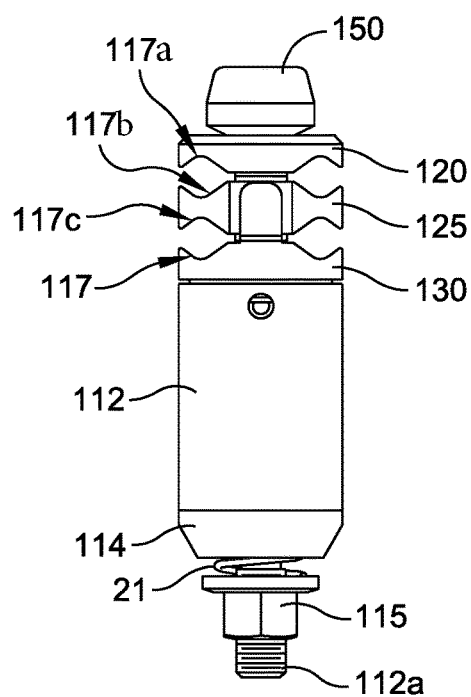
FIG. 7B is a side view of the clamp member of FIG. 7A viewed from a direction looking at an elevation view of a threaded elongated shaft that is engaged by the clamp member.
Figure 7C:
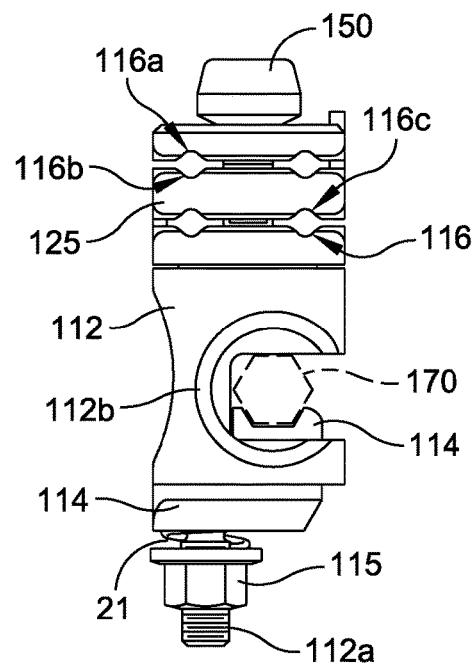
FIG. 7C is a side view of the clamp member of FIG. 7A viewed from a direction looking at an end of a threaded elongated shaft that is engaged by the clamp member.

In some embodiments, the main body portion 112 comprises a pin base plate 130 and the at least one first groove 116 are provided on the pin base plate 130 rather than directly on the main body portion 112 as described for the embodiment without the pin base plate 130. This example is illustrated in FIGS. 7A-7C.

Based on the structure of the clamp member 110A described herein, one can easily envision embodiments of a clamp, where more than two sets of bone fixation pins can be held by stacking additional intermediate pin cover plates between the main body portion 112 and the pin cover plate 120. Appropriate sets of grooves for receiving the bone fixation pins would be provided on the surfaces of the additional intermediate pin cover plates and the grooves that face each other to capture the bone fixation pins P would be aligned to each other.

Referring to FIGS. 8A-8F, according to some embodiments, the threaded C/D nut 200 comprises two portions 200A, 200B that are hinged together to split open for receiving the threaded elongated shaft 170 into its center opening 201. One of the two portions 200A is threaded internally, so when the two portions 200A, 200B are closed around the threaded elongated shaft 170, the two portions 200A, 200B form the center opening 201 in which the threaded elongated shaft 170 is held and the threaded internal surface 202 on the one portion 200A of the two portions 200A, 200B engage with the threads 175 on the elongated threaded shaft 170. Threading only one of the two portions is more cost efficient from manufacturing standpoint. The non-threaded side has an internal surface that is curved with a diameter that matches the major diameter of the threads 175. A hinge 204 connects the two portions 200A, 200B so that the two portions 200A, 200B can be spread open to engage (i.e., wrap around) the elongated shaft 170. A torsion spring 205 provided about the hinge 204 urges the two portions 200A, 200B into the closed configuration as the default configuration. This feature is also useful because it allows the threaded C/D nut 200 to grab on to the elongated shaft 170 and prevent it from falling off.

Figure 8C:
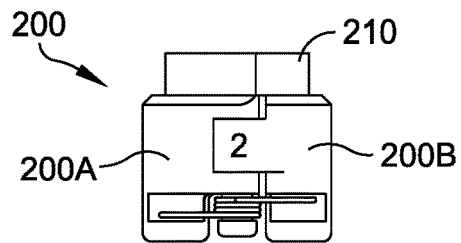
FIGS. 8A-8F are illustrations showing different views of a split compression/distraction nut of the bone fixation device.
Figure 8D:
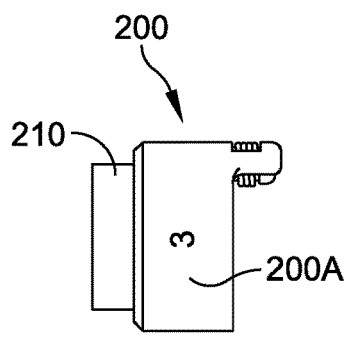
Figure 8A:
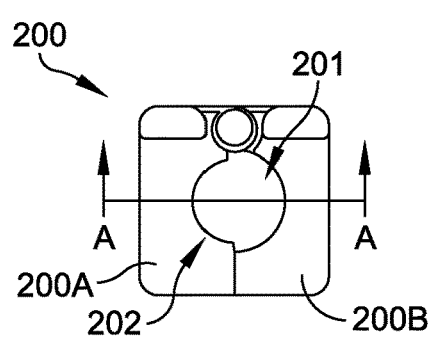
Figure 8B:
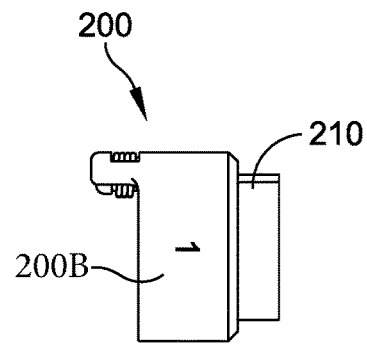
Figure 8E:
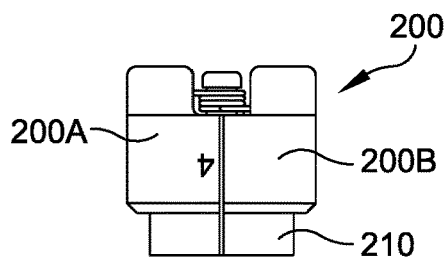
Figure 8F:
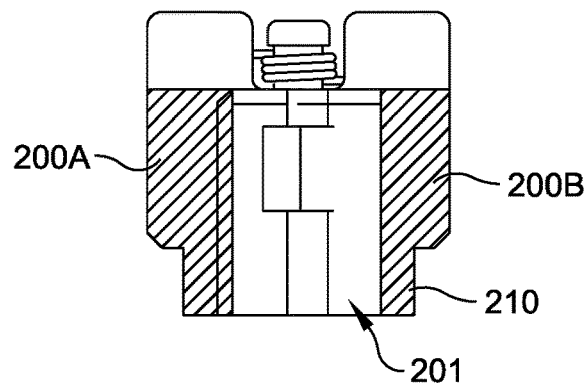

When in closed configuration, the threaded C/D nut 200 comprises am extended collar 210 portion that is sized and configured to rotatably engage the countersink 112b of the main body portion 112. The extended collar 210 extends into the countersink 112b while being engaged with the threaded elongated shaft 170. The extended collar 210 can prevent the split C/D nut 200 from popping open during the tightening procedure. As the threaded C/D nut 200 is turned in the direction on the elongated shaft 170 which moves the threaded C/D nut 200 towards the main body portion 112, the extended collar 210 extends into the countersink 112b and pushes the clamp member 110 along the elongated shaft 170. FIG. 8F is a sectional view of the threaded C/D nut 200 taken through the section line A-A in FIG. 8A. Therefore, in the configuration of the orthopedic device assembly 100 shown in FIGS. 1, 2A, and 4, one can adjust the distance between the two clamps 110 by turning the threaded C/D nut 200 on either of the two clamps 110.

FIGS. 9A-9F illustrate a non-splitting unitary threaded C/D nut 300 that can be used to threadedly engage the threaded elongated shaft 170 in place of the split threaded C/D nut 200, according to some embodiments. The threaded C/D nut 300 serves the same function as the threaded C/D nut 200. The threaded C/D nut 300 can be used to move the clamp member 110 along the threaded elongated shaft 170 same as the threaded nut 200. The threaded C/D nut 300 comprises a center opening 301 comprising an internal threaded surface 302 that threadedly engages the threads 175 of the threaded elongated shaft 170. The threaded C/D nut 300 also comprises an extended collar 310 that engages the main body portion 112 of the clamp member 110 by extending into the countersink 112b.

Although the devices, kits, systems, and methods have been described in terms of exemplary embodiments, they are not limited thereto. Rather, the appended claims should be construed broadly, to include other variants and embodiments of the devices, kits, systems, and methods, which may be made by those skilled in the art without departing from the scope and range of equivalents of the devices, kits, systems, and methods.

We claim:
1. An orthopedic device assembly comprising:
  a threaded elongated shaft comprising:
    a length;
    a longitudinal axis defined therethrough; and
    at least two flat threaded side surfaces extending over the length of the elongated shaft, wherein the at least two flat threaded side surfaces comprise threading extending the entirety of the at least two flat threaded side surfaces; and
  one or more clamp members configured to be releasably clamped on to the threaded elongated shaft,
  wherein when clamped on to the threaded elongated shaft, each of the one or more clamp members is configured for holding at least one bone fixation pin in an orientation that is non-parallel with the longitudinal axis of the elongated shaft and parallel to one of at least two flat threaded side surfaces of the elongated shaft, wherein each of the one or more clamp members is configured to be selectively rotated about the longitudinal axis of the elongated shaft, so that the bone fixation pins are parallel to a different one of the at least two flat threaded side surfaces of the elongated shaft, wherein each clamp member includes:

a main body portion;

a clamping piece, wherein the main body portion and the clamping piece form a channel that is sized for receiving the threaded elongated shaft and releasably clamping on to the elongated shaft; and a threaded nut provided at one end of the channel and rotatably engaging the main body, wherein the threaded nut is configured for threadably engaging the elongated shaft when the elongated shaft is clamped within the channel.

2. The assembly of claim 1, wherein the at least two flat threaded surfaces comprise six flat threaded surfaces.

3. The assembly of claim 1, wherein the main body portion and the clamping piece are configured to engage the profile of the elongated shaft.

4. The assembly of claim 3, wherein the clamping piece is spring-loaded for urging against one of the flat threaded surfaces on the threaded elongated shaft.

5. The assembly of claim 1, wherein the main body portion of the clamp comprises a countersink provided at one end of the channel for rotatably engaging the threaded nut.

6. An orthopedic device assembly comprising:

a threaded elongated shaft comprising:

a length;

a longitudinal axis defined therethrough; and at least two flat threaded side surfaces extending over the length of the elongated shaft, wherein the at least two flat threaded side surfaces comprise uninterrupted threading; and one or more clamp members configured to be releasably clamped on to the threaded elongated shaft, wherein when clamped on to the threaded elongated shaft, each of the one or more clamp members is configured for holding at least one bone fixation pin in an orientation that is non-parallel with the longitudinal axis of the elongated shaft and parallel to one of at least two flat threaded side surfaces of the elongated shaft, wherein each of the one or more clamp members is configured to be selectively rotated about the longitudinal axis of the elongated shaft, so that the bone fixation pins are parallel to a different one of the at least two flat threaded side surfaces of the elongated shaft, wherein each clamp member includes:

a main body portion;

a clamping piece, wherein the main body portion and the clamping piece form a channel that is sized for receiving the threaded elongated shaft and releasably clamping on to the elongated shaft; and a threaded nut provided at one end of the channel and rotatably engaging the main body, wherein the threaded nut is configured for threadably engaging the elongated shaft when the elongated shaft is clamped within the channel.

7. The assembly of claim 6, wherein the at least two flat threaded surfaces comprises six flat threaded surfaces.

8. The assembly of claim 6, wherein the main body portion and the clamping piece are configured to engage the profile of the elongated shaft.

9. The assembly of claim 8, wherein the clamping piece is spring-loaded for urging against one of the flat threaded surfaces on the threaded elongated shaft.

10. The assembly of claim 6, wherein the main body portion of the clamp comprises a countersink provided at one end of the channel for rotatably engaging the threaded nut.

11. An orthopedic device assembly comprising:

a threaded elongated shaft comprising:

a length;

a longitudinal axis defined therethrough; and at least two flat threaded side surfaces extending over the length of the elongated shaft, wherein the at least two flat threaded side surfaces comprise uninterrupted threading extending the entirety of the at least two flat threaded side surfaces; and one or more clamp members configured to be releasably clamped on to the threaded elongated shaft, wherein when clamped on to the threaded elongated shaft, each of the one or more clamp members is configured for holding at least one bone fixation pin in an orientation that is non-parallel with the longitudinal axis of the elongated shaft and parallel to one of at least two flat threaded side surfaces of the elongated shaft, wherein each of the one or more clamp members is configured to be selectively rotated about the longitudinal axis of the elongated shaft, so that the bone fixation pins are parallel to a different one of the at least two flat threaded side surfaces of the elongated shaft, wherein each clamp member includes:

a main body portion;

a clamping piece, wherein the main body portion and the clamping piece form a channel that is sized for receiving the threaded elongated shaft and releasably clamping on to the elongated shaft; and a threaded nut provided at one end of the channel and rotatably engaging the main body, wherein the threaded nut is configured for threadably engaging the elongated shaft when the elongated shaft is clamped within the channel.

12. The assembly of claim 11, wherein the at least two flat threaded surfaces comprises six flat threaded surfaces.

13. The assembly of claim 11, wherein the main body portion and the clamping piece are configured to engage the profile of the elongated shaft.

14. The assembly of claim 13, wherein the clamping piece is spring-loaded for urging against one of the flat threaded surfaces on the threaded elongated shaft.

15. The assembly of claim 11, wherein the main body portion of the clamp comprises a countersink provided at one end of the channel for rotatably engaging the threaded nut.

* * * * *